United States Patent [19]
Nakai et al.

[11] 3,966,899
[45] June 29, 1976

[54] METHOD OF TREATMENT OF MEDICINES

[76] Inventors: Yoshinobu Nakai, 2-5-2, Komagome, Toshima, Tokyo; Keiji Yamamoto, 10-510 Shiei Fuseko-Danchi, 206 Hieashi-Naebocho, Higashi, Sapporo, Hokkaido; Masahiro Nakano, 95-654-53, Hachiken, Nishi, Sapporo, Hokkaido, all of Japan

[22] Filed: Mar. 12, 1975

[21] Appl. No.: 557,696

[30] Foreign Application Priority Data
Sept. 13, 1974 Japan.............................. 49-104899

[52] U.S. Cl................................... 424/19; 259/1 R; 424/361; 241/27; 250/276
[51] Int. Cl.²............................................ A61J 3/00
[58] Field of Search ................. 259/1; 424/361, 19; 241/27; 250/273 (276)

[56] References Cited
UNITED STATES PATENTS

| | | | |
|---|---|---|---|
| 1,656,572 | 1/1928 | Schultze et al. | 264/109 |
| 2,337,915 | 12/1943 | Menger et al. | 264/109 |
| 2,347,638 | 4/1944 | McLachlan | 250/273 |
| 3,044,938 | 7/1962 | Halley | 424/19 |
| 3,713,593 | 1/1973 | Morris | 241/27 |

*Primary Examiner*—Lewis Gotts
*Assistant Examiner*—Cary Owens

[57] ABSTRACT

A method of manufacturing a pharmaceutical having a plurality of active ingredients so that each active ingredient will be released at substantially the same uniform rate involves mixing the active ingredients with beta-1, 4-glucan and pulverizing the mixture.

6 Claims, No Drawings

METHOD OF TREATMENT OF MEDICINES

This invention relates to a method for pharmaceutical manufacture whereby the rate of release of a sparingly soluble active ingredient from a medicine is regulated advantageously by use of beta-1, 4-glucan. More particularly, this invention relates to a method for pharmaceutical manufacture which comprises adding a plurality of active ingredients including one or more sparingly soluble active ingredients to beta-1, 4-glucan and simultaneously pulverizing the resultant mixture for thereby improving the rate of release of said active ingredients from all kinds of solid internal medicines in the form of powder, pellets, tablets, capsules, etc.

Where two or more active ingredients are mixed, their pharmacological activities may be manifested either synergistically or antagonistically, depending on the particular combination of active ingredients involved. These interactions of the ingredients in a medicine are called "synergistic or additive activity" and "antagonistic activity" respectively.

The pharmacological activity of an internal medicine is such that it is not manifested until after the medicine has been ingested into the living organism and assimilated as through the digestive tract into the body. As a natural consequence, the rate of its assimilation has a direct effect on the length of time during which the pharmacological activity is manifested. In case where a medicine containing a plurality of active ingredients is administered or different medicines are administered at a time, if the individual active ingredients contained therein dissolve at rates different from one another, then the actual effect of the administration may be reduced so much as to equal the effect attainable in the case of insufficient administration, although the prescription is such that the desired effect is obtained only when the active ingredients are assimilated altogether at the same time. Consequently, no curative effect can be expected of the administration. For many a medicine, therefore, it is desirable that all the active ingredients contained in the medicine are dissolved at one same rate within the digestive tract.

Conversely, there are times when a possible undesired secondary reaction is repressed by intentionally prescribing a medicine the active ingredients of which are of a combination such as to induce an antagonistic activity. In such a case, it is customary that only the active ingredients are prescribed in normal amounts and the other active ingredients incorporated for the purpose of repressing possible secondary reaction are prescribed in amounts a few times smaller than are usually used. Also in this case, all active ingredients incorporated to induce the antagonistic activity are desired to be released at one same rate, irrespectively of the concentrations in which they are included in the medicine to be administered.

In obtaining an expected curative effect, use of two or more active ingredients so selected as to provide a synergistic or additive activity proves to be more advantageous than use of only one active ingredient in a large dose, because the amounts of the plurality of active ingredients required are small so that otherwise possible manifestation of secondary reaction can be produced and excessive manifestation of medicinal effect can also be prevented. Even in this case, it is naturally desirable that the plurality of active ingredients expected to bring about the desired additive or synergistic activity be dissolved out of the medicine at a uniform rate.

In actuality, however, it is extremely difficult to effect prescription and pharmaceutical manufacture by making ideal use of such synergistic activity, additive activity or antagonistic activity.

For example, active ingredients have widely different characteristics such that they can be classified by degree of solubility under the sparingly soluble group and the readily soluble group or by form under the solid group and the liquid group. Accordingly, it is quite difficult for active ingredients of so widely different properties to be released at one same rate from a given medicine. In the case of a sparingly soluble active ingredient available in the form of a solid powder, it may be comminuted further to a finer particle size or it may be converted into the form of a salt readily soluble in water so as to enhance the rate of dissolution of the active ingredient. In many cases, such measure proves to be inadequate and is not always practicable. In case efforts are made to attain a desired curative effect by use of a synergistic activity, for example, two or more active ingredients involved in the prescription often dissolve at rates different from one another. Such being the case, efforts are made toward uniformization of the rates of release of a plurality of active ingredients from a given medicine as by carrying out a preliminary in-vitro or in-vivo test on each active ingredient and, depending on the results of the preliminary test, decreasing the particle size of a less easily soluble solid active ingredient to such an extent as to equalize the rate of dissolution with that of other active ingredients. In spite of these efforts, it frequently seems to be difficult to equalize the rates of dissolution of all the active ingredients involved. Even when the rates of dissolution of active ingredients used in a given medicine are managed to be equalized, it is not necessarily improbable that the equalized rate of release will be changed when a prescription happens to require use of this medicine in combination with some other medicine.

From the standpoint of techniques of pharmacy of prescription, there has been felt the need for development of a method of pharmaceutical manufacture capable of providing a medicine which comprises a plurality of active ingredients and which, upon administration to a patient, permits each active ingredient to be released therefrom at a uniform rate.

An approach made to this problem as described herein below has enabled the inventors to find a successful solution thereto.

The experimental observations in which the present invention originates will be described briefly.

A water-soluble ingredient and a sparingly soluble ingredeint were mixed with beta-1, 4-glucan which had been comminuted and rendered amorphous in advance by means of a vibrating mill and the resultant mixture was blended and pulverized. Pyridoxine hydrochloride was used as to water-soluble ingredient and phenacetin as the sparingly soluble ingredient. The mixing ratio of the two drugs to beta-1, 4-glucan was so fixed that 10 parts of pyridoxine hydrochorlide and 5 to 50 parts of phenacetin were incorporated per 100 parts of beta-1, 4-glucan. The test specimen obtained by the pulverization of the mixture was tested for release of two active ingredients in water as the solvent. In the test, both pyridoxine hydrochloride and phenacetin showed outstanding releasability such that a release rate of as much as more than 80% was observed at the end of 10 minutes standing.

In contrast, in the case of a test specimen obtained by pulverizing pyridoxine hydrochloride, phenacetin and beta-1, 4-glucan independently of one another and then subjecting them to simple mixing, pyridoxine hydrochloride which is a watersoluble ingredient showed a release rate of more than 80% within 10 minutes of standing whereas phenacetin showed a release rate of only 20% in 10 minutes and 50% in 60 minutes.

In the case of a test specimen obtained by simultaneously pulverizing beta-1, 4-glucan and phenacetin and adding to the resultant mixture preparatorily comminuted pyridoxine hydrochloride, the release rate of two active ingredients was only 40% in 10 minutes and 70% in 60 minutes.

As concerns the effect of the amount of phenacetin added upon the rate of release, the release rate was substantially invariable so far as the concentration of phenacetin was up to the level of 25% by weight based on beta-1, 4-glucan and it tended to decline somewhat as the concentration increased over the level.

As is clear from the foregoing test observation, if in a medicine comprising phenacetin and another active ingredient, these active ingredients are comminuted simultaneously with beta-1, 4-glucan, there is provided an extremely high release rate compared with a medicine of the same composition prepared by having phenacetin alone pulverized simultaneously with beta-1, 4-glucan. This observation has implied possibility of an epochal method for pharmaceutical manufacture capable of uniformizing the rates of release of all active ingredients from a medicine comprising of two or more active ingredients and, consequently, improving the curative effect of the medicine.

An elaborate view of the foregoing test results has led to the following discovery. A study was carried out concerning active ingredients which, in a medicine prepared through simultaneous pulverization with beta-1, 4-glucan, provides inferior solubility in water. Caffeine was used in place of pyridoxine hydrochloride. In a small ball mill, 10 parts of phenacetin, 5 parts of caffeine and beta-1, 4-glucan were placed and simultaneously pulverized until the diffraction peak brought about by the presence of a crystalline structure ceased to appear in the X-ray diffraction diagram. Then the resultant mixture was tested for releasability of two active ingredients from the medicine.

The test showed that both phenacetin and caffeine were released quickly at a uniform rate of 60% in 10 minutes and 90% in 60 minutes. In the case of a test specimen obtained by having caffeine and phenacetin pulverized independently of each other in advance and simply mixing the resultant ingredients with preparatorily comminuted beta-1, 4-glucan, the release rate of phenacetin was 20% in 10 minutes and 50% in 60 minutes and that of caffeine was 30% in 10 minutes and 70% in 60 minutes, indicating a heavy difference between the rates of release. When the three-component systems of caffeine, phenacetin and beta-1, 4-glucan was further mixed with aminopyrine and the resultant mixture was simultaneously pulverized, the rate of release of the active ingredients from the resulting medicine was high and uniform as compared with a test specimen prepared by having the same active ingredients pulverized independently of one another in advance and then simply mixing the resultant mixture with preparatorily comminuted beta-1, 4-glucan. This clearly indicated the advantage of the method of simultaneous mixing as it is applied to compound medicines prescribed for additive or synergistic activity of the all active ingredients involved. It has thus been demonstrated that the simultaneous mixing with beta-1, 4-glucan permits all active ingredients to be released at one same rate from the resultant medicine, no matter whether there are used two or more active ingredients or whether water-soluble active ingredients and water-insoluble active ingredients are in coexistance and that the rate of release is higher than when a medicine is prepared by subjecting its active ingredients to simple mixing.

In effecting the simultaneous pulverization with beta-1, 4-glucan, the method of pulverization is not exclusive: The effect of uniformization and acceleration of the release rate is invariable when prescribed amounts of phenacetin, caffeine and aminopyrine are simultaneously added to and then pulverized simultaneously with finely divided beta-1, 4-glucan, when beta-1, 4-glucan and only phenacetin, for exaample, are simultaneously pulverized, then caffeine and aminopyrine are added thereto and the resultant four-component mixture is continuously subjected to the pulverization treatment and when the active ingredients are added, all at once or successively one after another, to preparatorily commununed beta-1, 4-glucan and subjecting the resultant mixture to simultaneous mixing. The time for the simultaneous pulverization is variable with the particular kind of the pulverizing machine to be used, the amount of the ingredients used, the magnitude of power employed for pulverization, etc., it is generally of the order of several hours. The simultaneous pulverization is only required to be continued until the diffraction peak characteristic of a crystalline substance ceases to be detectable in the X-ray diffraction performed by the ordinary reflection method or penetration method. Any pulverization continued beyond this level only means loss of energy and does not contribute to productivity and rather entails a possibility of degrading the properties of active ingredients being treated. If the simultaneous pulverization is stopped before all active ingredients are completely deprived of crystallinity, namely, while the X-ray diffraction peak is still recognizable, the effect aimed at by the present invention is decreased by the extent to which the time of pulverization is curtailed. As regards the apparatus to be used for the pulverization, it has been confirmed that any mechanism capable of accomplishing required fine pulverization by mechanical crushing or attrition can freely be selected. Examples are a rotary ball mill, a vibrating ball mill, a shaker mill and a hammer mill. The pulverization may be carried out by use of a ball mill of an airtight construction, for example. The atmosphere within the closed ball mill in which the mixed ingredients are simultaneously pulverized may be maintained under a continuous flow of such inert gas as nitrogen gas, helium gas or argon gas or said atmosphere may be formed by displacing the interior air of the ball mill in advance with such inert gas so as to ensure stability of the active ingredients which are otherwise susceptible to oxidation and other undesirable reactions. This method may be adopted as one advantageous measure for the working of this invention.

In the case of the four-component medicine consisting of beta-1, 4-glutan, phenacetin, caffeine and aminopyrine, it has been learned that the change in the mixing ratio of the active ingredients to beta-1, 4-glucan has the following effect on the release rate of the active ingredients from the medicine.

The three active ingredients and beta-1, 4-glucan were mixed at varying ratios shown in Table 1 and then subjected to simultaneous pulverization. When the resultant test specimens were tested for release rate, there were obtained results which are shown in the lower section of Table 1.

which is accomplished invariably with all the different active ingredients being subjected to simultaneous pulverization with beta-1, 4-glucan.

Similar observations to those described so far were made when various sparingly soluble active ingredients were mixed with water-soluble active ingredients or other sparingly soluble active ingredients and then pulverized simultaneously with beta-1, 4-glucan. Examples of the active ingredients which, through simulta- Table 1

Effect of mixing ratio of active ingredients

| Time of standing | Mixing ratio of active ingredients (amount, in parts; added per 100 parts of beta 1, 4-glucan) | | | | | | | | | | | |
|---|---|---|---|---|---|---|---|---|---|---|---|---|
| | a | | | b | | | c | | | d | | |
| | (ph) | (Ca) | (Am) | (ph) | (Ca) | (Am) | (ph) | (Ca) | (Am) | (ph) | (Ca) | (Am) |
| | 30 | 10 | 20 | 120 | 40 | 80 | 1200 | 400 | 800 | 30 | 10 | 20 |
| 10 minutes | ≥60% | ≥60% | ≥60% | ≥60% | ≥60% | ≥60% | ≥55% | ≥55% | ≥55% | 20% | 30% | 25% |
| 60 minutes | ≥90% | ≥90% | ≥90% | ≥90% | ≥90% | ≥90% | ≥80% | ≥80% | ≥80% | 50% | 70% | 60% |

Note (1) Medium of dissolution: Water
(2) (BG): Abbreviation for beta-1, 4-clucan
(Ca): Abbreviation for caffeine
(ph): Abbreviation for phenacetin
(Am): Abbreviation for aminopyrine
(3) d = Test specimen prepared by having (BG), (ph), (Ca) and (Am) pulverized independently of one another in advance and then simply mixing prescribed amounts thereof. This is cited for control sample with the test specimens a, b and c.

From the test results given above, it can be concluded that neither upper limit nor lower limit exists for the mixing ratio of the active ingredients to beta-1, 4-glucan from the practical point of view. In the case of a medicine containing the active ingredients in small amounts, for example, the phenomenon of the release of active ingredients from the medicine proceeds in a more effective direction. Even in the case of a medicine containing the active ingredients in large amounts, the rate of release is notably large as compared with the comparative medicine in which the ingredients each in a finely comminuted form are simply mixed with one another.

The substantial uniformization and acceleration of the release rate which is brought about by the simultaneous pulverization of the active ingredients with beta-1, 4-glucan may possibly be explained by a postulate such as is given herein below. In the case of ordinary crystalline active ingredients, when the active ingredients are subjected to a pulverizing force, the particles of the active ingredients undergo fine size reduction in the initial stage of pulverization. Application of further pulverizing force beyond this level only serves to bring about the so-called state of mechanochemical equilibrium in which the cohesion caused by the intermolecular force is balanced with the beating force creased by the external mechanical pulverizing force, rendering it increasingly more difficult to effect thorough elimination of the crystallinity of active ingredients. When the active ingredients are pulverized simultaneously with beta-1, 4-glucan, beta-1, 4-glucan is caused to intervene among the particles of active ingredients being pulverized and therefore serves to impede otherwise possible generation of cohesion between the adjacent particles of the active ingredients and consequently precludes the occurrence of the state of mechanochemical equilibrium, permitting the elimination of the cyrstallinity of active ingredients to be effected till perfection. The increased release rate of active ingredients from the resultant medicine is believed to be ascribable to this perfect elimination of crystallinity neous pulverization with beta-1, 4-glucan, produce medicines enjoying improved and uniformed release rates compared with their countertypes prepared through independent pulverization and simple mixing are: Antifebric analgestic drugs, drugs for nuerotic disorders, sedative narcotic drugs, muscular relaxants, blood pressure depressors and antihistamine drugs such as caffeine, camphor, quinine, calcium gluconate, dimethyl caprol, sulfamine, theophylline, theobromine, riboflavin, mephenesin, phenobarbital, aminopyrine, thioacetazone, quercetin, rutin, salicilic acid, sodium theophyline, pyrabital, quinine hydrochloride, irgapyrine, digitoxin and glyceofluvin, antibiotics such as acetylspiramycin, ampicillin, erythromycin, xathamycin, chloramphenicol, triacetyloleandomycin, nystatin, colistin sulfate and various sparingly soluble salts of these antibiotics. Other examples are steriod hormon type medicines such as methyltestosterone, methylanthrosterone diol, progesterone, estrandiol benzoate, ethynylesteradiol, desoxycorticosterone acetate, cortisone acetate, hydrocortisone, hydrocortisone acetate and prednisolon, and nonsteroidic ovarian hormon type medicines such as dienesterol, hexasterol, diethylstylbene sterol dipropionate and chlorostrianisene. By the application of the method of this invention directed to the improvement and uniformation of release rate, pharmaceutical manufacture designs aimed at synergistic activity, additive activity or antagonistic activity can easily and safely be accomplished by following prescriptions involving such sparingly soluble active ingredients and utilizing one or a plurality of water-soluble and/or sparingly soluble active ingredients. (See Examples 1 and 2.)

The product of the simultaneous pulverization of active ingredients with beta-1, 4-glucan to be obtained as described above may, where necessary, be mixed at a suitable ratio with an excipient, a flowability improver, disintegrator, a binder or other active ingredients for the preparation of a powder medicine, a capsule medicine or a tableted medicine by an ordinary method.

When a specimen produced by mixing and pulverizing the active ingredients as indicated in Example 5 in accordance with the present invention is subjected to wet granulation and then compressed by an ordinary rotary tableting machine, the resultant medicine provides a high and uniformized release rate as compared with a medicine prepared by simply pulverizing the active ingredients.

The term "beta-1, 4-glucan" as used in the present invention refers to a product manufactured from a raw material which is a vegatable-active ingredient-containing cellulose as by means of chemical decomposition, mechanical disintegration, ultrasonic waves or irradiation of high energy electron beams such as of gamma rays. The chemical decomposition may be carried out by any of the known methods. The mechanical disintegration may freely be accomplished by means of a ball mill, a hammer mill, a tube mill, a vibrating mill or some other crushing or attriting machine in either a wet or dry process. The size reduction of the cellulosic substance by means of ultrasonic waves or by irradiation of high energy electron beams may be effected by the method suggested by F. M. Morehead (Textile Research Journal, August 1950, pp. 549–553) or by the method proposed by Imamura, Murakami et al (Journal of Textile Science Society, Tokyo, Vol. 15, No. 11, 1959). These methods are not necessarily the only ones that are available for the purpose.

EXAMPLE 1

With 8 g of beta-1, 4-glucan, 1 g of tetracycline hydrochloride as a water-soluble antibiotic preparation and 1 g of phenoxymethyl penicillin (penicillin V) which is held to manifest an antagonistic activity against said antibiotic preparation were mixed. The mixture was sealed in a stainless steel shaker mill and pulverized. The shaker mill had an inner volume of 38 cc and contained 17 balls each measuring 11 mm in diamter. The time for the pulverization was determined by a preliminary test which was performed until crystalline particles ceased to exist and be detectable in the X-ray diffraction diagram. It was found to be 8 hours. Typical conditions adopted for the measurement of X-ray diffraction were as follows:

| Target | Cu | Filter | Ni |
|---|---|---|---|
| Voltage | 30 KV | Current | 10 mA |
| Count range | 250 cps | Time const. | 2 sec. |
| Scanning speed | 2°/min | Chart speed | 40 mm/min |

An X-ray diffraction recorder was used as the X-ray diffraction apparatus.

For the determination of the release rate of active ingredients from the medicine prepared by mixing and simultaneous pulverization, 1 g of the powdered test specimen was placed in a beaker having an inner volume of 300 cc and a solvent was poured thereon. A stirrer was inserted in the contents of the beaker and rotated at a fixed rate. At fixed intervals, the contents were sampled and each specimen thus taken was passed through a glass filter to remove comminuted beta-1, 4-glucan and obtain a liquid in which the active ingredients released from the mixed preparation were contained. By using a double-beam U.V. spectrophotometer, the specimen was tested for tetracycline hydrochloride and phenoxymethyl penicillin absorption spectra at $\lambda = 220$ mu and $\lambda = 274$ mu respectively, with their concentration calculated by means of the calibration curve method.

The determination was carried out in a constant temperature bath regulated at $25° \pm 0.1°C$, with 250 cc of 0.1 N hydrochloric acid used as the solvent.

The rate of release thus determined was more than 80% of tetracycline hydrochloride and more than 80% of phenoxymethyl penicillin at the end of 10 minutes agitation. The total release after 60 minutes of agitation was more than 95% for both the ingredients.

Separately, beta-1, 4-glucan tetracycline hydrochloride and phenoxymethyl penicillin were pulverized independently of one another and the resultant powders were mixed at a weight ratio of 8:1:1. When the specimen thus obtained was subjected to the same release test as described above, the release rate at the end of 10 minutes agitation was more than 80% of tetracycline hydrochloride and 30% of phenoxymethyl penicillin and the total release after 60 minutes of agitation was more than 95% of tetracycline hydrochloride and only 55% of phenoxymethyl penicillin.

The comparison ascertains that the simultaneous pulverization of ingredients with beta-1, 4-glucan provided by the present invention is effective in uniformizing and improving the rate of release of such ingredients from the medicine.

EXAMPLE 2

With 50 g of beta-1, 4-glucan were mixed 100 g of cortisone acetate which is a sparingly soluble steriod hormone type ingredient capable of anti-inflammation activity and 50 g of phenolbarbital which is a sparingly soluble ingredient serving to improve the metabolism of said hormon. The resultant mixture was charged in a rotary ball mill having an inner volume of 5 liters and pulverized for 12 hours until the contents were rendered completely amorphous.

Two (2) g of the pulverized specimen was placed in a beaker having an inner volume of 500 ml and held in a constant temperature bath kept at $20° \pm 0.1°C$ and 400 ml of pure water adjusted in advance to 20°C was poured on the specimen. The contents of the beaker were agitated at a fixed rate of rotation and sampled at fixed intervals. A 50-ml specimen was taken each after 10 minutes and 60 minutes of agitation. The specimen was passed through a filter paper to be deprived of insolubles. The filtrate was evaporated under a water bath and then left to stand for 3 days within a pressure-reduced desiccator containing therein silica gel intended for moisture absorption to ensure perfect desiccation of the evaporated specimen.

The dry specimen was dissolved in 100 ml of added ethanol. Accurately 5 ml of the resultant solution was measured out and diluted with additionally introduced ethanol to a total volume of 25 ml. The diluted solution was tested by the ultraviolet spectrophotometry for cortisone acetate absorption spectrum at $\lambda = 238$ mu, with its concentration calculated by the calibration curve method.

From the remaining 95 ml of ethanol solution, a 50-ml portion was taken and titrated for pheno barbital content by 0.1-N sodium hydroxide with thymolphthalein used as the indicator.

In the case of a preparation obtained by simultaneous pulverization with beta-1, 4-glucan, the release rate at the end of 10 minutes and 60 minutes agitation was 75% and 92% respectively for both cortisone acetate and phenobarbital.

In contrast, in the case of a preparation obtained by having the three components pulverized independently of one another and then simply mixed with one another, the release rate was 30% of cortisone acetate and 35% of phenobarbitol after 10 minutes of agitation and 50% of the former and 60% of the latter after 60 minutes of agitation.

EXAMPLE 3

By following the procedure of Example 1, tetracycline hydrochloride and phenoxymethyl penicillin were simultaneously pulverized for ten hours with beta-1, 4-glucan at mixing ratios shown in Table 2.

The pulverized specimens thus obtained were subjected to release test by using 0.1N hydrochloric acid solution as the solvent. The results of this test were as shown in Table 3.

Table 2

| | Mixing ratio (parts) | | |
|---|---|---|---|
| No. | (BG) | (Te) | (ph) |
| 1 | 1.00 | 0.05 | 0.01 |
| 2 | 1.00 | 0.50 | 0.10 |
| 3 | 1.00 | 5.00 | 1.00 |
| 4 | 1.00 | 50.00 | 10.00 |

(Note) BG: Abbreviation for beta-1, 4-glucan
Te: Abbreviation for tetracycline hydrochloride
ph: Abbreviation for phenoxymethyl penicillin Table 3

| | Release rate Release rate (minutes) | | | |
|---|---|---|---|---|
| | 10 | | 60 | |
| | (Te) | (ph) | (Te) | (ph) |
| 1 | $\geq 80\%$ | $\geq 80\%$ | $\geq 95\%$ | $\geq 95\%$ |
| 2 | $\geq 80\%$ | $\geq 80$ | $\geq 95$ | $\geq 95$ |
| 3 | $\geq 80\%$ | $\geq 80$ | $\geq 95$ | $\geq 95$ |
| 4 | $\geq 80\%$ | $\geq 75$ | $\geq 95$ | $\geq 90$ |
| 5 | $\geq 80\%$ | $\geq 35$ | $\geq 95$ | $\geq 60$ |

(Note) No. 5 represents a preparation obtained by pulverizing the three components independently and simply mixing the resultant powders at the rate of (BG):(Te):(ph) = 1:0.05:0.01.

EXAMPLE 4

With 200 g of the product of simultaneous pulverization with beta-1, 4-glucan obtained in Example 2 were uniformly mixed 100 g of DVM 80-mesh lactose, 25 g of corn starch, 25 g of beta-1, 4-glucan and 2 g of magnesium stearate. The resultant mixture was tableted by direct compaction on a rotary tableting machine. The rotary tableting machine was operated with the compression pressure fixed at 400 kg/cm$^2$ and the disk rotation rate at 20 rpm respectively. In the machine, the mortar contained standard concaves 8 mm in diamter, with the tablet weight regulated to 200 mg. The tablet thus produced had a hardness of 15 kg and a disintegration time in water of 10 minutes. The weight dispersion among the tablets was 2.5%. All these values pass the specifications by the Japanese Pharmacopoeia.

As a control, a preparation was obtained by pulverizing cortisone acetate, phenobarital and beta-1, 4-glucan independently of one another and simply mixing the resultant powders. The preparation was mixed with excipients and lubricants in the same way as described above and the resultant mixture was tableted by direct compression. The tablets had a hardness of 14 kg, a disintegration time in water of 9 minutes and a weight deviation of 2.8%. The values pass the specifications by the Japanese Pharmacopoeia.

The two kinds of tablets produced as described above were subjected to release test after the manner described in Example 2. The results of the test were as shown in the following table. It is seen from this table that the tablets produced through the simultaneous pulverization with beta-1, 4-glucan showed higher rates of release, indicating that the method of this invention permits manufacture of medicines with improved uniform release of active ingredients.

| | Rate of release | | | |
|---|---|---|---|---|
| Time of agitation | Medicine obtained by simultaneous pulverization | | Medicine obtained by simple mixing | |
| | (Co) | (ph) | (Co) | (ph) |
| 5 minutes | $\geq 60\%$ | $\geq 60\%$ | 10% | 15% |
| 10 minutes | $\geq 70$ | $\geq 70$ | 25 | 30 |
| 60 minutes | $\geq 90$ | $\geq 90$ | 45 | 50 |

(Note) Co: Cortisone acetate ph: phenobarbital

As a control, 250 g of a preparation was obtained by pulverizing beta-1, 4-glucan, cortisone acetate and phenobarbital independently of one another in advance and mixing the resultant powders at the same mixing ratio as mentioned above. The preparation was mixed similarly with lactose and corn starch and subjected to wet granulation and then mixed with added magnesium stearate. The mixture was then tableted. The tablets thus produced were found to have a hardness of 16 kg, a disintegration time in water of 48 minutes and a weight deviation of 2.1%.

The two kinds of tablets produced by the aforementioned procedure were subjected to a release test. It was consequently ascertained that the tablets produced through the simultaneous pulverization with beta-1, 4-glucan showed a release rate four to six times as high after 10 minutes of agitation and two to one and a half times as high after 60 minutes of agitation respectively as the release rate obtained for the control. Moreover, both cortisone acetate and phenobarbital were seen to be released at the same rate.

From the results, it may be concluded that the present invention permits manufacture of medicines capable of providing a quick release of active ingredients and therefore warranting a desirable pharmacological activity. From the results of the present example, it is judged that the same pharmacological effect is obtained when the medicines are manufactured directly by the wet granulation method and administered in the form of granules and when the granules thus obtained are encapsulated and administered in the form of capsules.

EXAMPLE 5

With 250 g of the product of simultaneous pulverization with beta-1, 4-glucan obtained by following the procedure of Example 2 were mixed with 100 g. of ordinary lactose and 50 g of corn starch. The resultant mixture was mixed with 12 g of calcuim carboxymethyl cellulose as a disintegrating agent and 160 g of 2% starch solution as a binder for seven minutes in a planetary mixer and then pulverized and granulated by means of a speed mill. The wet granules thus obtained were left to stand in a hot air drier overnight at 40°C. The dry granules were screened through a 16 mesh and a 60 mesh sieve. The granules of particle size fraction between 16 mesh pass and 60 mesh stop was mixed with 0.5% by weight of magnesium stearate and tried to be tableted after the manner of Example 4.

The tablets thus produced had a hardness of 17 kg, a disintegration time in water of 5 minutes and a weight deviation of 2.0%. These values pass the specifications of the Japanese Pharmacopoeia.

Having thus described the invention, what is claimed is:

1. The method of manufacturing a pharmaceutical comprising a plurality of pharmacologically active ingredients whereby upon administration to a patient each active ingredient will be released therefrom at substantially the same uniform rate, said method consisting essentially of mixing a plurality of pharmacologically active ingredients with beta-1, 4-glucan, and pulverizing the mixture.

2. The method of claim 1 wherein at least one of the active ingredients is sparingly soluble.

3. The method of claim 1 wherein at least one of the active ingredients is water-soluble.

4. The method of claim 1 wherein pulverization is carried to the extent that diffraction peak characteristics of any crystalline substance ceases to be detectable by X-ray diffraction techniques.

5. The method of claim 1 including the additional step of incorporating the pulverized mixture into a solid pharmaceutical dosage form.

6. The method of claim 1 including the additional step of compacting the pulverized mixture into a tablet.

* * * * *

UNITED STATES PATENT OFFICE
CERTIFICATE OF CORRECTION

PATENT NO. : 3,966,899
DATED : June 29, 1976
INVENTOR(S) : Nakai et al.

It is certified that error appears in the above-identified patent and that said Letters Patent are hereby corrected as shown below:

```
Col. 1, line 65  "produced" should read    --precluded--
Col. 2, line 62  "hydrochorlide" should read  --hydrochloride--
Col. 3, line  7  "watersoluble" should read   --water-soluble--
Col. 3, line 25  "communited" should read   --comminuted--
Col. 3, line 33  "of" first occurrence should be deleted
Col. 3, line 36  "view" should read   --review--
Col. 3, line 40  "provides" should read   --provide--
Col. 4, line 27  "commununted" should read --comminuted--
Col. 4, line 67  "glutan" should read   --glucan--
Col. 6, line 28  "uniformed" should read   --uniformized--
Col. 6, line 32  "nuerotic" should read   --neurotic--
Col. 6, line 53  "uniformation" should read   --uniformization--
Col. 7, line 40  "diamter" should read --diameter--
Col. 9, line  5  "phenobarbitol" should read   --phenobarbital--
Col. 9, line 48  "DVM" should read   --DMV--
Col. 9, line 56  "diamter" should read --diameter--
Col. 9, line 57  "tablet" should read --tablets--
```

Signed and Sealed this

Fourteenth Day of September 1976

[SEAL]

Attest:

RUTH C. MASON
Attesting Officer

C. MARSHALL DANN
Commissioner of Patents and Trademarks